United States Patent [19]

Asada et al.

[11] Patent Number: 5,366,883
[45] Date of Patent: Nov. 22, 1994

[54] α-AMYLASE GENE

[75] Inventors: Kiyozo Asada; Takashi Uemori; Hiroyuki Mukai, all of Shiga; Ikunoshin Kato, Kyoto, all of Japan; Kenneth Laderman; Christian B. Anfinsen, both of Baltimore, Md.

[73] Assignees: Takara Shuzo Co., Ltd., Kyoto, Japan; The Johns Hopkins University, Baltimore, Md.

[21] Appl. No.: 894,212

[22] Filed: Jun. 9, 1992

[51] Int. Cl.⁵ ............ C12N 15/56; C12N 15/63; C12N 15/75; C12N 1/21
[52] U.S. Cl. ............ 435/202; 435/69.1; 435/71.2; 435/240.2; 435/252.3; 435/252.33; 435/252.31; 435/320.1; 536/23.2; 536/23.1; 935/14; 935/29; 935/56; 935/72; 935/73; 935/74
[58] Field of Search ............ 435/69.1, 71.2, 240.2, 435/252.3, 252.33, 252.31, 320.1, 202; 536/27, 23.2, 23.1

[56] References Cited

FOREIGN PATENT DOCUMENTS 9011352 10/1990 WIPO .

OTHER PUBLICATIONS

Cowan et al. Trends in Biotechnology 10:315-323 (1992).
Saiki et al. Int. J. Systematic Biology 33(3) 253-259 (1985).
A. Belyavsky et al. "PCR-based cDNA library construction . . . " Nuc. Acids. Res. 17(8) 2919-2932 (Apr. 1989).
S. Fukusumi et al. "Cloning and Nucleotide Sequence of a heat . . . " Eur. J. Biochem. 174:15-21 (May 1988).
R. Koch et al. "Extremely thermostable amylolyhi enzyme . . . " FEMS Microbiol. Lett. 71:21-26 (Sep. 1990).
S. L. Berger et al. (eds.) "Guide to Molecular Cloning Techniques." Meth. in Enzymol. vol. 132:393-399, 415-423, 432-447, 661-704 (1987).
M. P. Deutscher (ed.) "Guide to Protein Purification" Meth. in Enzymol. vol. 182:602-613, 738-751 (1990).
Koch, "Purification and properties of a hyperthermoactive α-amylase from the archaebacterium Pyrococcus woesei", Arch. Microbiol. (1991) 155:572-578.
Brown et al, "Characerization of Amylolytic Enzyme Activities Associated with the Hyperthermophilic Archaebacterium *Pyrococcus furiosus*", Applied and Environmental Microbiology, Jul. 1990, pp. 1985-1991.

Primary Examiner—Robert A. Wax
Assistant Examiner—Rebecca Prouty
Attorney, Agent, or Firm—Cushman, Darby & Cushman

[57] ABSTRACT

The present invention relates, in general, to a cloned α-amylase gene, and, in particular, to a cloned hyperthermophilic α-amylase gene and to methods of producing α-amylase using same.

13 Claims, 9 Drawing Sheets

FIG. 1A

```
  1        C TGC AGG GGA GTT TGC AAA GCT AAT AAC TTC AGT AGC    61
           TGG TGG AGG AGG CGG AGG AAG AAA

62   AGA ACT AGC TCA AGG TAA GAT AAG AGA CAT AGA AAA AGC     124
      AAA AGA GGC AAT AGA AAA AGT TAA

125   GGG CTC TCT ATA GCT TTC TAC TCT CCT TCT TTT GGA ATC     187
      AGA AAT ATT TCA TAT TCT GAT CTC

188   CAG AAT GGG AGC TTG TTC ATC TTT ATT TTT ATA TAA TAC     250
      TCG GTG CTT TCT CTG TAT ATT

251   TTC TCC ACT ACT TCC TGG GGC AGT TGG AAC TGA ACT ATA     313
      ATT TCA GCA TCC TCT GAT AAC TTT

314   GTT TCA AAT TTT GAA GTA CCC TTG TAA TCC TTT CCA TTT
      ACC TTT ATG AGA TAA TTT GTG CCC

377   TCT GGA AAT TCT ATT TCG AAG TTG AAA TCT GAG ACA ATT     439
      TTT TCC ACT TTT AGC GTA AAT AAC

440   CCC CAA CCG TCT TTT TCA ACT ATT GTA ACT GTC CTG TTT     502
      TCC TTA TAG AAT ATC TCA CCT GAT

503   TCT TTT TCA TTA ATG GTT GCA GGA GGC ATT TTT GCC GTT     565
      CTC ATG GCA AGC ACT AGA AGG ACT

566   ATA AAA ATT ATT GCT ACA GCT GTT ATT TTC TTG TCC ATG     628
      CTA ACA CCC TGT AAT GAG ATT TGG

629   ATT TTC CTA TAT AAA AAG CCT TAG TTA TTT TTG AGC CAT     691
      TAA ATA TAT AAG GAA GTA TCA CTC
```

FIG. 1B

```
  1                                                              D   K   I
        N   F   I   F   G   I   H   N                            D   K   I
692    TTA GTG ATT AAT GGG TGG ACG GAA GTG GGA GAT AAA ATT        11
       AAC TTC ATA TTT GGA ATT CAC AAC                           754

12     H   Q   P   L   G   N   F   G   W   V   F   E   E
755    CAT CAG CCC CTG GGC AAC TTT GGA TGG GTG TTT GAG GAG        32
        A   Y   E   K   C   Y   W   P                            817
       GCT TAT GAA AAG TGT TAC TGG CCG

33     F   L   E   T   L   E   E   Y   P   N   M   K   V
818    TTT CTG GAG ACT CTG GAG GAA TAT CCA AAC ATG AAG GTT        53
        A   I   H   T   S   G   P   L                            880
       GCC ATT CAT ACA AGT GGC CCC CTC

54     I   E   W   L   Q   D   N   R   P   E   Y   I   D
881    ATT GAG TGG CTC CAA GAT AAT AGA CCC GAA TAC ATA GAC        74
        L   L   R   S   L   V   K   R                            943
       TTG CTT AGA AGT CTA GTG AAA AGA

75     G   Q   Q   V   E   I   V   A   G   F   Y   E   P
944    GGA CAG CAG GTG GAG ATA GTC GTT GCT GGG TTC TAC GAG CCT    95
        V   L   A   S   I   P   K   E                           1006
       GTG CTA GCA TCA ATC CCA AAG GAA

96     D   R   I   E   Q   I   R   L   M   K   E   W   A
1007   GAT AGA ATA GAG CAG ATA AGG TTA ATG AAA GAG TGG GCT       116
        K   S   I   G   F   D   A   R                          1069
       AAG AGT ATT GGA TTT GAT GCT AGG

117     G   V   W   L   T   E   R   V   W   Q   P   E   L
1070   GGA GTT TGG CTA ACT GAA AGA GTA TGG CAA CCA GAG CTC       137
        V   K   T   L   K   E   S   G                          1132
       GTA AAG ACC CTT AAG GAG AGC GGA
```

FIG. IC

```
138    I   D   Y   V   I   V   D   D   Y   H   F   M   S                158
1133  ATA GAT TAT GTA ATA GTT GAC GAT TAC CAC TTC ATG AGT               1195
       A   G   L   S   K   E   E   L
      GCG GAA TTA AGT AAA GAG GAG CTG

159    Y   W   P   Y   Y   T   E   D   G   G   E   V   I                179
1196  TAC TGG CCA TAT TAT ACG GAA GAT GGT GGG GAA GTT ATA               1258
       A   V   F   P   I   D   E   K
      GCT GTT TTC CCG ATA GAT GAG AAG

180    L   R   Y   L   I   P   F   R   P   V   D   K   V                200
1259  TTG AGA TAT TTG ATT CCC TTT AGA CCC GTT GAT AAG GTC               1321
       L   E   Y   H   S   L   I
      TTA GAA TAC CTG CAT TCT CTC ATA

201    D   G   D   E   S   K   V   A   V   F   H   D   D                221
1322  GAT GGT GAT GAG AGC AAA GTT GCA GTA TTT CAT GAC GAT               1384
       G   E   K   F   G   I   W   P
      GGT GAG AAG TTT GGA ATC TGG CCT

222    G   T   Y   E   W   V   Y   E   K   G   W   L   R                242
1385  GGA ACT TAT GAG TGG GTG TAT GAA AAG GGA TGG TTA AGA               1447
       E   F   F   D   R   I   S
      GAA TTC TTT GAT AGA ATT TCA AGT

243    D   E   K   K   I   N   L   M   L   Y   T   E   Y   L            263
1448  GAT GAA AAG AAG ATA AAC TTA ATG CTT TAC ACT GAA TAC TTA           1510
       E   K   Y   K   P   R   G   L
      GAA AAA TAT AAG CCT AGA GGT CTT

264    V   Y   L   P   I   A   S   Y   F   E   M   S   E              284
1511  GTT TAT CTT CCA ATA GCT TCA TAT TTT GAG ATG AGC GAA              1573
       W   S   L   P   A   K   Q   A
      TGG TCA TTG CCA GCA AAG CAG GCA
```

FIG. 1D

```
      R   L   F   V   E   F   V   N  'E   L   K   V   K   305
285   AGG CTC TTT GTG GAG TTC GTC AAT GAG CTT AAA GTT AAA
1574      G   I   F   E   K   Y   R   V                  1636
      GGT ATA TTT GAA AAG TAC AGG GTA

F   V   R   G   G   I   W   K   N   F   F   Y   K   326
306   TTT GTT AGG GGA GGA ATT TGG AAG AAT TTC TTC TAT AAA
1637      Y   P   E   S   N   Y   M   H                  1699
      TAC CCA GAG AGC AAC TAC ATG CAC

K   R   M   L   M   V   S   K   L   V   R   N   N   347
327   AAG AGA ATG CTA ATG GTA AGT AAG TTA GTG AGA AAC AAT
1700                                                      1762

P   E   A   R   K   Y   L   L                  F   368
348   CCT GAG GCC AGG AAG TAT CTG CTG                 TTC
1763  R   A   Q   C   N   D   A   Y   W   H   G   L   F
      AGA GCA CAA TGT AAC GAT GCT TAT TGG CAC GGC CTC TTC
      G   G   V   Y   L   P   H   L
      GGT GGA GTA TAT TTA CCC CAT CTT

R   R   A   I   W   N   N   L   I   K   A   N   S   389
369   AGG AGG GCC ATC TGG AAC AAT TTA ATC AAG GCC AAC AGC
1826      Y   V   S   L   G   K   V   I                  1888
      TAT GTA AGC CTT GGA AAG GTC ATA

R   D   I   D   Y   D   G   D   F   E   E   V   L   I   410
390   AGG GAT ATC GAC TAC GAT GGC TTT GAG GAA GTT CTC ATA
1889      E   N   D   N   F   Y   A   V                      1951
      GAG AAT GAC AAC TTT TAT GCA GTG
```

FIG. IE

```
411         F   K   P   S   Y   G   S   L   V   E   F   S    431
1952       TTT AAA CCC TCT TAC GGT TCC TTG GTG GAG TTT TCA
            S   K   N   R           Y
           TCA AAG AAT AGA         TAT                       2014

432         V   D   V   L   A   R   W   E   H   Y   H   G    452
2015       GTA GAT GTT CTG GCA AGA AGG TGG GAA CAC TAT CAT GGC
            Y   V   E   S   Q   F   D
           TAT GTG GAA AGT CAA TTT GAT GGA                   2077

453         V   A   S   I   H   E   L   E   K   K   I   P   D   473
2078       GTA GCC AGC ATT CAT GAG CTC GAG AAA AAG ATA CCA GAT
            E   I   R   K   E   V   A   Y
           GAA ATA AGA AAA GAA GTT GCT TAC                   2140

474         D   K   Y   R   R   F   M   L   Q   D   H   V    494
2141       GAC AAG TAC AGA AGG TCC ATG CTT CAA GAT CAC GTC
            P   L   G   T   T   L   E   D
           CCC CTG GGA ACA ACT CTG GAA GAC                   2203

495         F   M   F   S   R   Q   Q   E   I   G   E   F   P   515
2204       TTC ATG TTC TCA AGA CAA CAG GAG ATC GGA GAG TTT CCT
            R   V   P   Y   S   Y   E   L
           AGG GTT CCA TAC TCA TAT GAA CTA                   2266

516         L   D   G   G   I   R   L   K   R   E   H   L   G   536
2267       CTA GAT GGA GGA ATA AGG CTG AAG AGG GAA CAC TTG GGA
            I   E   V   E   K   T   V   K
           ATA GAA GTT GAA AAA ACA GTG AAG                   2329
```

FIG. 1F

```
537          L   V   N   D   G   F   E   V   E   Y   I   V   N      557
2330        TTA GTG AAT GAT GGA TTT GAG GTG GAG TAT ATA GTG AAC      2392
             N   K   T   G   N   P   V   L
            AAC AAG ACA GGA AAT CCT GTA TTG

558          F   A   V   E   L   N   V   A   V   Q   S   I   M      578
2393        TTC GCA GTG GAA CTT AAC GTT GCA GTT CAG AGC ATA ATG      2455
             E   S   P   G   V   L   R   G
            GAG AGC CCA GGA GTT CTA AGG GGG

579          K   E   I   V   V   D   K   Y   A   V   G   K          599
2456        AAA GAA ATT GTC GTT GAT AAG TAT GCA GTT GGG AAG          2518

F   A   L   K   F   E   D   E
            TTT GCA CTG AAG TTT GAA GAC GAA

600          M   E   V   W   K   Y   P   V   K   T   L   S   Q      620
2519        ATG GAA GTC TGG AAG TAT CCA GTA AAG ACT CTC AGT CAA      2581
             S   E   S   G   W   D   L   I
            AGT GAA AGT GGC TGG GAT CTA ATC

621          Q   Q   G   V   S   Y   I   V   P   I   R   L   E      641
2582        CAG CAG GGT GTC AGC TAC ATA GTT CCA ATA AGG TTG GAG      2644
             D   K   I   R   F   K   L   K
            GAT AAA ATA AGG TTT AAG CTA AAA

642          F   E   E   A   S   G                                  647
2645        TTT GAG GAA GCC TCG GGA TAG GGA GGC CCT CAT CAC CAA      2707
            TCA GGG CCC GAA AGA CTC CCT CAT
```

FIG. IG

```
2708  CGG CCC TTC TAT TTT ATT TTA AAC GTC AAT GGT TTA CCA
      AGT TTC CAA AAC TTA CAA AAT GAA                     2770

2771  CAA ATC TCT CCA CTT GCG GGC ATT CCA CAT ATC TTG CAC
      TCT TTG AGG TCT TTC ACT                             2833

2834  TCT GGC TCG AAA AGT TTT CTT AGG AAT CCT CTC
      ACG AAG TTG AAC TTT GTT CCA GGC                     2896

2897  CTT TTT TCC TCC AAT TCA TTG AGA ACT TCC TTC ATG TCA
      AGA GTT GTC GCA CCT CTT GCA TAA                     2959

2960  GGA CAC TCC TCT ACT ATG TAC TCC AAT CCA ACG GCA ATG
      GCA TAG GCA ACA ACT TCC CTC TCA                     3022

3023  GTT AAT TCG TAG AGA GGT TTG ATC TTC TTT ACG AAC TTT
      CCT TCC CCT GGG AGC AGA GGA CCT                     3085

3086  CCC TTA GCC AGG TAC TCT GTA TTC CAG TGG AGT AAG TTG
      TTC ATG AGA AAG CTT                                 3139
```

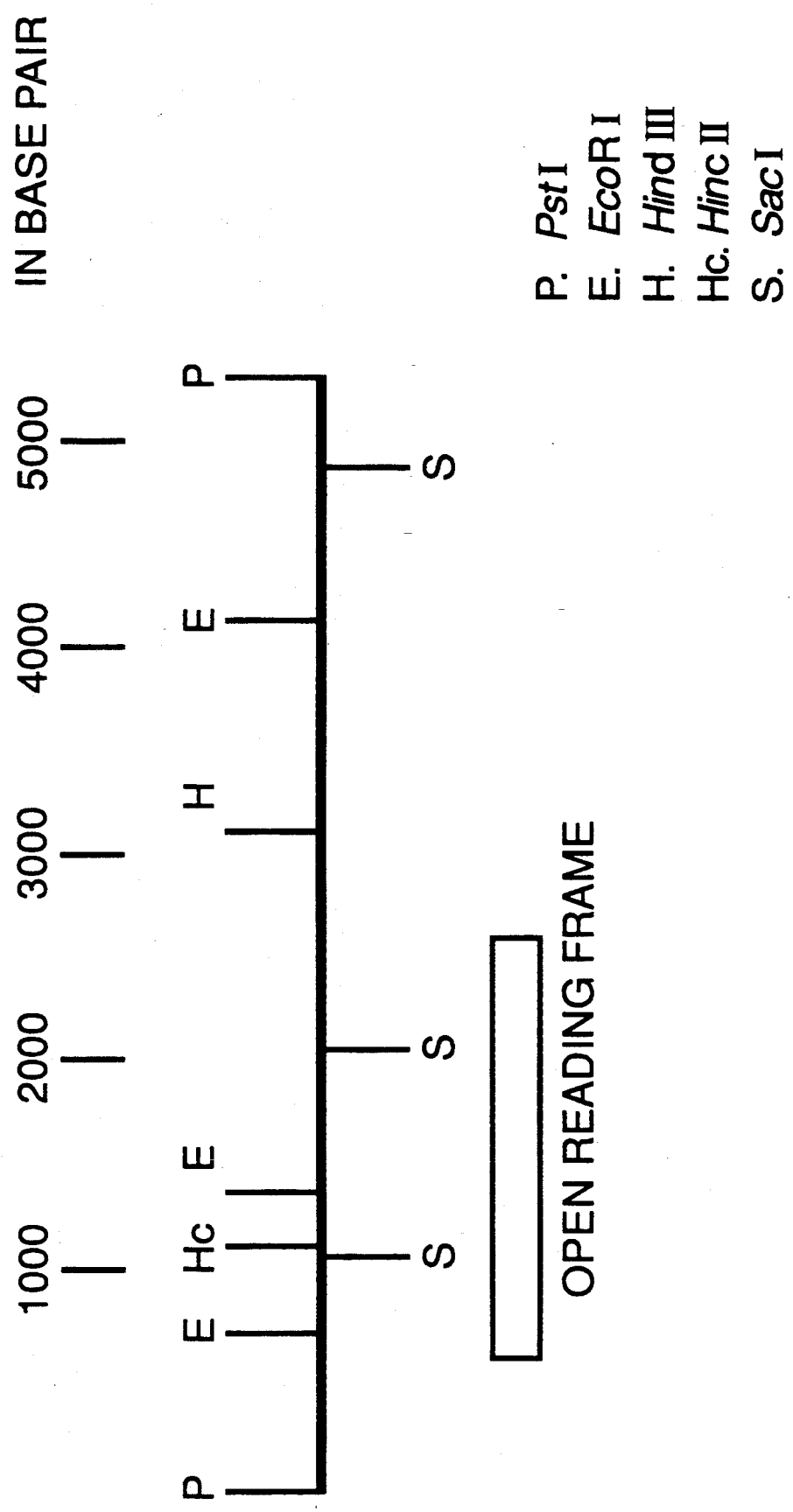

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 3139 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

| | | | | | |
|---|---|---|---|---|---|
| CTGCAGGGGA | GTTTGCAAAG | CTAATAACTT | CAGTAGCTGG | TGGAGGAGGC | GGAGGAAGAA | 60 |
| AAGAACTAGC | TCAAGGTAAG | ATAAGAGACA | TAGAAAAAGC | AAAAGAGGCA | ATAGAAAAAG | 120 |
| TTAAGGGCTC | TCTATAGCTT | TCTACTCTCC | TTCTTTTGGA | ATCAGAAATA | TTTCATATTC | 180 |
| TGATCTCCAG | AATGGGAGCT | TGTTCATCTT | TATTTTTATA | TAATACTCGG | TGCTTTTCTC | 240 |
| TCTGTATATT | TTCTCCACTA | CTTCCTGGGG | CAGTTGGAAC | TGAACTATAA | TTTCAGCATC | 300 |
| CTCTGATACC | TTTGTTTCAA | ATTTTGAAGT | ACCCTTGTAA | TCCTTTCCAT | TTACCTTTAT | 360 |
| GAGATAATTT | GTGCCCTCTG | GAAATTCTAT | TTCGAAGTTG | AAATCTGAGA | CAATTTTTC | 420 |
| CACTTTTAGC | GTAAATAACC | CCCAACCGTC | TTTTCAACT | ATTGTAACTG | TCCTGTTTTC | 480 |
| CTTATAGAAT | ATCTCACTTG | ATTCTTTTC | ATTAATGGTT | GCAGGAGGCA | TTTTTGCCGT | 540 |
| TCTCATGGCA | AGCACTAGAA | GGACTATAAA | AATTATTGCT | ACAGCTGTTA | TTTTCTTGTC | 600 |
| CATGCTAACA | CCCTGTAATG | AGATTTGGAT | TTTCCTATAT | AAAAGCCTT | AGTTATTTT | 660 |
| GAGCCATTAA | ATATATAAGG | AAGTATCACT | CTTAGTGATT | AATGGGTGGA | CGGAAGTGGG | 720 |
| AGATAAAATT | AACTTCATAT | TTGGAATTCA | CAACCATCAG | CCCCTGGGCA | ACTTTGGATG | 780 |
| GGTGTTTGAG | GAGGCTTATG | AAAAGTGTTA | CTGGCCGTTT | CTGGAGACTC | TGGAGGAATA | 840 |
| TCCAAACATG | AAGGTTGCCA | TTCATACAAG | TGGCCCCCTC | ATTGAGTGGC | TCCAAGATAA | 900 |
| TAGACCCGAA | TACATAGACT | TGCTTAGAAG | TCTAGTGAAA | AGAGGACAGG | TGGAGATAGT | 960 |
| CGTTGCTGGG | TTCTACGAGC | CTGTGCTAGC | ATCAATCCCA | AAGGAAGATA | GAATAGAGCA | 1020 |
| GATAAGGTTA | ATGAAAGAGT | GGGCTAAGAG | TATTGGATTT | GATGCTAGGG | GAGTTTGGCT | 1080 |
| AACTGAAAGA | GTATGGCAAC | CAGAGCTCGT | AAAGACCCTT | AAGGAGAGCG | AATAGATTA | 1140 |
| TGTAATAGTT | GACGATTACC | ACTTCATGAG | TGCGGGATTA | AGTAAAGAGG | AGCTGTACTG | 1200 |
| GCCATATTAT | ACGGAAGATG | GTGGGGAAGT | TATAGCTGTT | TTCCGATAG | ATGAAGTT | 1260 |
| GAGATATTTG | ATTCCCTTTA | GACCCGTTGA | TAAGGTCTTA | GAATACCTGC | ATTCTCTCAT | 1320 |
| AGATGGTGAT | GAGAGCAAAG | TTGCAGTATT | TCATGACGAT | GGTGAGAAGT | TTGGAATCTG | 1380 |
| GCCTGGAACT | TATGAGTGGG | TGTATGAAAA | GGGATGGTTA | AGAGAATTCT | TGATAGAAT | 1440 |
| TTCAAGTGAT | GAAAAGATAA | ACTTAATGCT | TTACACTGAA | TACTTAGAAA | AATATAAGCC | 1500 |
| TAGAGGTCTT | GTTTATCTTC | CAATAGCTTC | ATATTTGAG | ATGAGCGAAT | GGTCATTGCC | 1560 |
| AGCAAAGCAG | GCAAGGCTCT | TTGTGGAGTT | CGTCAATGAG | CTTAAAGTTA | AAGGTATATT | 1620 |
| TGAAAAGTAC | AGGGTATTTG | TTAGGGGAGG | AATTTGGAAG | AATTCTTCT | ATAAATACCC | 1680 |
| AGAGAGCAAC | TACATGCACA | AGAGAATGCT | AATGGTAAGT | AAGTTAGTGA | GAAACAATCC | 1740 |
| TGAGGCCAGG | AAGTATCTGC | TGAGAGCACA | ATGTAACGAT | GCTTATTGGC | ACGGCCTCTT | 1800 |
| CGGTGGAGTA | TATTTACCCC | ATCTTAGGAG | GGCCATCTGG | AACAATTTAA | TCAAGGCCAA | 1860 |
| CAGCTATGTA | AGCCTTGGAA | AGGTCATAAG | GGATATCGAC | TACGATGGCT | TTGAGGAAGT | 1920 |
| TCTCATAGAG | AATGACAACT | TTTATGCAGT | GTTTAAACCC | TCTTACGGTG | GTTCCTTGGT | 1980 |
| GGAGTTTTCA | TCAAAGAATA | GACTCGTGAA | TTATGTAGAT | GTTCTGGCAA | GAAGGTGGGA | 2040 |
| ACACTATCAT | GGCTATGTGG | AAAGTCAATT | TGATGGAGTA | GCCAGCATTC | ATGAGCTCGA | 2100 |
| GAAAAGATA | CCAGATGAAA | TAAGAAAAGA | AGTTGCTTAC | GACAAGTACA | GAAGGTTCAT | 2160 |
| GCTTCAAGAT | CACGTAGTCC | CCCTGGGAAC | AACTCTGGAA | GACTTCATGT | TCTCAAGACA | 2220 |
| ACAGGAGATC | GGAGAGTTTC | CTAGGGTTCC | ATACTCATAT | GAACTACTAG | ATGGAGGAAT | 2280 |
| AAGGCTGAAG | AGGGAACACT | TGGGAATAGA | AGTTGAAAAA | ACAGTGAAGT | TAGTGAATGA | 2340 |

-continued

```
TGGATTTGAG GTGGAGTATA TAGTGAACAA CAAGACAGGA AATCCTGTAT TGTTCGCAGT      2400

GGAACTTAAC GTTGCAGTTC AGAGCATAAT GGAGAGCCCA GGAGTTCTAA GGGGGAAAGA      2460

AATTGTCGTT GATGACAAGT ATGCAGTTGG GAAGTTTGCA CTGAAGTTTG AAGACGAAAT      2520

GGAAGTCTGG AAGTATCCAG TAAAGACTCT CAGTCAAAGT GAAAGTGGCT GGGATCTAAT      2580

CCAGCAGGGT GTCAGCTACA TAGTTCCAAT AAGGTTGGAG GATAAAATAA GGTTTAAGCT      2640

AAAATTTGAG GAAGCCTCGG GATAGGGAGG CCCTCATCAC CAATCAGGGC CGAAAGACT       2700

CCCTCATCGG CCCTTCTATT TTATTTTAAA CGTCAATGGT TTACCAAGTT TCCAAAACTT      2760

ACAAAATGAA CAAATCTCTC CACTTGCGGG CATTCCACAT ATCTTGCACT CTTTGAGGTC      2820

TTTCCCCTTC ACTTCTGGCT CGAAAAGTTT TTTCTTTCTT AGGAATCCTC TCACGAAGTT      2880

GAACTTTGTT CCAGGCCTTT TTTCCTCCAA TTCATTGAGA ACTTCCTTCA TGTCAAGAGT      2940

TGTCGCACCT CTTGCATAAG GACACTCCTC TACTATGTAC TCCAATCCAA CGGCAATGGC      3000

ATAGGCAACA ACTTCCCTCT CAGTTAATTC GTAGAGAGGT TTGATCTTCT TTACGAACTT      3060

TCCTTCCCCT GGGAGCAGAG GACCTCCCTT AGCCAGGTAC TCTGTATTCC AGTGGAGTAA      3120

GTTGTTCATG AGAAAGCTT                                                   3139
```

(2) INFORMATION FOR SEQ ID NO:2:

(i) SEQUENCE CHARACTERISTICS:
        (A) LENGTH: 649 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Gly Asp Lys Ile Asn Phe Ile Phe Gly Ile His Asn His Gln Pro
 1               5                  10                  15

Leu Gly Asn Phe Gly Trp Val Phe Glu Glu Ala Tyr Glu Lys Cys Tyr
                20                  25                  30

Trp Pro Phe Leu Glu Thr Leu Glu Glu Tyr Pro Asn Met Lys Val Ala
            35                  40                  45

Ile His Thr Ser Gly Pro Leu Ile Glu Trp Leu Gln Asp Asn Arg Pro
        50                  55                  60

Glu Tyr Ile Asp Leu Leu Arg Ser Leu Val Lys Arg Gly Gln Val Glu
 65                  70                  75                  80

Ile Val Val Ala Gly Phe Tyr Glu Pro Val Leu Ala Ser Ile Pro Lys
                85                  90                  95

Glu Asp Arg Ile Glu Gln Ile Arg Leu Met Lys Glu Trp Ala Lys Ser
                100                 105                 110

Ile Gly Phe Asp Ala Arg Gly Val Trp Leu Thr Glu Arg Val Trp Gln
            115                 120                 125

Pro Glu Leu Val Lys Thr Leu Lys Glu Ser Gly Ile Asp Tyr Val Ile
        130                 135                 140

Val Asp Asp Tyr His Phe Met Ser Ala Gly Leu Ser Lys Glu Glu Leu
145                 150                 155                 160

Tyr Trp Pro Tyr Tyr Thr Glu Asp Gly Glu Val Ile Ala Val Phe
                165                 170                 175

Pro Ile Asp Glu Lys Leu Arg Tyr Leu Ile Pro Phe Arg Pro Val Asp
            180                 185                 190

Lys Val Leu Glu Tyr Leu His Ser Leu Ile Asp Gly Asp Glu Ser Lys
                195                 200                 205

Val Ala Val Phe His Asp Asp Gly Glu Lys Phe Gly Ile Trp Pro Gly
        210                 215                 220
```

| | | | | | | | | | | | | | | |
|---|---|---|---|---|---|---|---|---|---|---|---|---|---|---|
| Thr | Tyr | Glu | Trp | Val | Tyr | Glu | Lys | Gly | Trp | Leu | Arg | Glu | Phe | Phe | Asp |
| 225 | | | | | 230 | | | | 235 | | | | | | 240 |
| Arg | Ile | Ser | Ser | Asp | Glu | Lys | Ile | Asn | Leu | Met | Leu | Tyr | Thr | Glu | Tyr |
| | | | | 245 | | | | | 250 | | | | | 255 | |
| Leu | Glu | Lys | Tyr | Lys | Pro | Arg | Gly | Leu | Val | Tyr | Leu | Pro | Ile | Ala | Ser |
| | | | 260 | | | | | 265 | | | | | 270 | | |
| Tyr | Phe | Glu | Met | Ser | Glu | Trp | Ser | Leu | Pro | Ala | Lys | Gln | Ala | Arg | Leu |
| | | 275 | | | | | 280 | | | | | 285 | | | |
| Phe | Val | Glu | Phe | Val | Asn | Glu | Leu | Lys | Val | Lys | Gly | Ile | Phe | Glu | Lys |
| | 290 | | | | | 295 | | | | | 300 | | | | |
| Tyr | Arg | Val | Phe | Val | Arg | Gly | Gly | Ile | Trp | Lys | Asn | Phe | Phe | Tyr | Lys |
| 305 | | | | | 310 | | | | | 315 | | | | | 320 |
| Tyr | Pro | Glu | Ser | Asn | Tyr | Met | His | Lys | Arg | Met | Leu | Met | Val | Ser | Lys |
| | | | | 325 | | | | | 330 | | | | | 335 | |
| Leu | Val | Arg | Asn | Asn | Pro | Glu | Ala | Arg | Lys | Tyr | Leu | Leu | Arg | Ala | Gln |
| | | | 340 | | | | | 345 | | | | | 350 | | |
| Cys | Asn | Asp | Ala | Tyr | Trp | His | Gly | Leu | Phe | Gly | Gly | Val | Tyr | Leu | Pro |
| | | 355 | | | | | 360 | | | | | 365 | | | |
| His | Leu | Arg | Arg | Ala | Ile | Trp | Asn | Asn | Leu | Ile | Lys | Ala | Asn | Ser | Tyr |
| | 370 | | | | | 375 | | | | | 380 | | | | |
| Val | Ser | Leu | Gly | Lys | Val | Ile | Arg | Asp | Ile | Asp | Tyr | Asp | Gly | Phe | Glu |
| 385 | | | | | 390 | | | | | 395 | | | | | 400 |
| Glu | Val | Leu | Ile | Glu | Asn | Asp | Asn | Phe | Tyr | Ala | Val | Phe | Lys | Pro | Ser |
| | | | | 405 | | | | | 410 | | | | | 415 | |
| Tyr | Gly | Gly | Ser | Leu | Val | Glu | Phe | Ser | Ser | Lys | Asn | Arg | Leu | Val | Asn |
| | | | 420 | | | | | 425 | | | | | 430 | | |
| Tyr | Val | Asp | Val | Leu | Ala | Arg | Arg | Trp | Glu | His | Tyr | His | Gly | Tyr | Val |
| | | 435 | | | | | 440 | | | | | 445 | | | |
| Glu | Ser | Gln | Phe | Asp | Gly | Val | Ala | Ser | Ile | His | Glu | Leu | Glu | Lys | Lys |
| | 450 | | | | | 455 | | | | | 460 | | | | |
| Ile | Pro | Asp | Glu | Ile | Arg | Lys | Glu | Val | Ala | Tyr | Asp | Lys | Tyr | Arg | Arg |
| 465 | | | | | 470 | | | | | 475 | | | | | 480 |
| Phe | Met | Leu | Gln | Asp | His | Val | Val | Pro | Leu | Gly | Thr | Thr | Leu | Glu | Asp |
| | | | | 485 | | | | | 490 | | | | | 495 | |
| Phe | Met | Phe | Ser | Arg | Gln | Gln | Glu | Ile | Gly | Glu | Phe | Pro | Arg | Val | Pro |
| | | | 500 | | | | | 505 | | | | | 510 | | |
| Tyr | Ser | Tyr | Glu | Leu | Leu | Asp | Gly | Gly | Ile | Arg | Leu | Lys | Arg | Glu | His |
| | | 515 | | | | | 520 | | | | | 525 | | | |
| Leu | Gly | Ile | Glu | Val | Glu | Lys | Thr | Val | Lys | Leu | Val | Asn | Asp | Gly | Phe |
| | 530 | | | | | 535 | | | | | 540 | | | | |
| Glu | Val | Glu | Tyr | Ile | Val | Asn | Asn | Lys | Thr | Gly | Asn | Pro | Val | Leu | Phe |
| 545 | | | | | 550 | | | | | 555 | | | | | 560 |
| Ala | Val | Glu | Leu | Asn | Val | Ala | Val | Gln | Ser | Ile | Met | Glu | Ser | Pro | Gly |
| | | | | 565 | | | | | 570 | | | | | 575 | |
| Val | Leu | Arg | Gly | Lys | Glu | Ile | Val | Val | Asp | Asp | Lys | Tyr | Ala | Val | Gly |
| | | | 580 | | | | | 585 | | | | | 590 | | |
| Lys | Phe | Ala | Leu | Lys | Phe | Glu | Asp | Glu | Met | Glu | Val | Trp | Lys | Tyr | Pro |
| | | 595 | | | | | 600 | | | | | 605 | | | |
| Val | Lys | Thr | Leu | Ser | Gln | Ser | Glu | Ser | Gly | Trp | Asp | Leu | Ile | Gln | Gln |
| | 610 | | | | | 615 | | | | | 620 | | | | |
| Gly | Val | Ser | Tyr | Ile | Val | Pro | Ile | Arg | Leu | Glu | Asp | Lys | Ile | Arg | Phe |
| 625 | | | | | 630 | | | | | 635 | | | | | 640 |
| Lys | Leu | Lys | Phe | Glu | Glu | Ala | Ser | Gly | | | | | | | |
| | | | | 645 | | | | | | | | | | | |

( 2 ) INFORMATION FOR SEQ ID NO:3:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Asp Lys Ile Asn Phe Ile Phe Gly Ile His Asn His Gln Pro Leu Gly
1               5                   10                  15
Asn
```

( 2 ) INFORMATION FOR SEQ ID NO:4:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Thr Leu Asn Asp Met Arg Gln Glu Tyr Tyr Phe Lys
1               5                   10
```

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

GAYAARATHA AYTTYATHTT                                     20

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

YGGNATHCAY AAYCAYCARC C                                   21

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

YTTRAARTAR TAYTCYTGNC KCATRT CRTT                         30

( 2 ) INFORMATION FOR SEQ ID NO:8:

( i ) SEQUENCE CHARACTERISTICS:
    ( A ) LENGTH: 647 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:8:

```
Asp Lys Ile Asn Phe Ile Phe Gly Ile His Asn His Gln Pro Leu Gly
 1               5                  10                  15

Asn Phe Gly Trp Val Phe Glu Glu Ala Tyr Glu Lys Cys Tyr Trp Pro
            20                  25                  30

Phe Leu Glu Thr Leu Glu Glu Tyr Pro Asn Met Lys Val Ala Ile His
        35                  40                  45

Thr Ser Gly Pro Leu Ile Glu Trp Leu Gln Asp Asn Arg Pro Glu Tyr
     50                  55                  60

Ile Asp Leu Leu Arg Ser Leu Val Lys Arg Gly Gln Val Glu Ile Val
 65                  70                  75                  80

Val Ala Gly Phe Tyr Glu Pro Val Leu Ala Ser Ile Pro Lys Glu Asp
                85                  90                  95

Arg Ile Glu Gln Ile Arg Leu Met Lys Glu Trp Ala Lys Ser Ile Gly
                100                 105                 110

Phe Asp Ala Arg Gly Val Trp Leu Thr Glu Arg Val Trp Gln Pro Glu
            115                 120                 125

Leu Val Lys Thr Leu Lys Glu Ser Gly Ile Asp Tyr Val Ile Val Asp
    130                 135                 140

Asp Tyr His Phe Met Ser Ala Gly Leu Ser Lys Glu Glu Leu Tyr Trp
145                 150                 155                 160

Pro Tyr Tyr Thr Glu Asp Gly Glu Val Ile Ala Val Phe Pro Ile
                165                 170                 175

Asp Glu Lys Leu Arg Tyr Leu Ile Pro Phe Arg Pro Val Asp Lys Val
            180                 185                 190

Leu Glu Tyr Leu His Ser Leu Ile Asp Gly Asp Glu Ser Lys Val Ala
            195                 200                 205

Val Phe His Asp Asp Gly Glu Lys Phe Gly Ile Trp Pro Gly Thr Tyr
    210                 215                 220

Glu Trp Val Tyr Glu Lys Gly Trp Leu Arg Glu Phe Phe Asp Arg Ile
225                 230                 235                 240

Ser Ser Asp Glu Lys Ile Asn Leu Met Leu Tyr Thr Glu Tyr Leu Glu
            245                 250                 255

Lys Tyr Lys Pro Arg Gly Leu Val Tyr Leu Pro Ile Ala Ser Tyr Phe
            260                 265                 270

Glu Met Ser Glu Trp Ser Leu Pro Ala Lys Gln Ala Arg Leu Phe Val
        275                 280                 285

Glu Phe Val Asn Glu Leu Lys Val Lys Gly Ile Phe Glu Lys Tyr Arg
    290                 295                 300

Val Phe Val Arg Gly Gly Ile Trp Lys Asn Phe Phe Tyr Lys Tyr Pro
305                 310                 315                 320

Glu Ser Asn Tyr Met His Lys Arg Met Leu Met Val Ser Lys Leu Val
                325                 330                 335

Arg Asn Asn Pro Glu Ala Arg Lys Tyr Leu Leu Arg Ala Gln Cys Asn
            340                 345                 350

Asp Ala Tyr Trp His Gly Leu Phe Gly Gly Val Tyr Leu Pro His Leu
        355                 360                 365

Arg Arg Ala Ile Trp Asn Asn Leu Ile Lys Ala Asn Ser Tyr Val Ser
370                 375                 380
```

|     |     |     |     |     |     |     |     |     |     |     |     |     |     |     |     |
|---|---|---|---|---|---|---|---|---|---|---|---|---|---|---|---|
| Leu 385 | Gly | Lys | Val | Ile | Arg 390 | Asp | Ile | Asp | Tyr | Asp 395 | Gly | Phe | Glu | Glu | Val 400 |
| Leu | Ile | Glu | Asn | Asp 405 | Asn | Phe | Tyr | Ala | Val 410 | Phe | Lys | Pro | Ser | Tyr 415 | Gly |
| Gly | Ser | Leu | Val 420 | Glu | Phe | Ser | Ser | Lys 425 | Asn | Arg | Leu | Val | Asn 430 | Tyr | Val |
| Asp | Val | Leu 435 | Ala | Arg | Arg | Trp | Glu 440 | His | Tyr | His | Gly | Tyr 445 | Val | Glu | Ser |
| Gln | Phe 450 | Asp | Gly | Val | Ala | Ser 455 | Ile | His | Glu | Leu | Glu 460 | Lys | Lys | Ile | Pro |
| Asp 465 | Glu | Ile | Arg | Lys | Glu 470 | Val | Ala | Tyr | Asp | Lys 475 | Tyr | Arg | Arg | Phe | Met 480 |
| Leu | Gln | Asp | His | Val 485 | Val | Pro | Leu | Gly | Thr 490 | Thr | Leu | Glu | Asp | Phe 495 | Met |
| Phe | Ser | Arg | Gln 500 | Gln | Glu | Ile | Gly | Glu 505 | Phe | Pro | Arg | Val | Pro 510 | Tyr | Ser |
| Tyr | Glu | Leu 515 | Leu | Asp | Gly | Gly | Ile 520 | Arg | Leu | Lys | Arg | Glu 525 | His | Leu | Gly |
| Ile | Glu 530 | Val | Glu | Lys | Thr | Val 535 | Lys | Leu | Val | Asn | Asp 540 | Gly | Phe | Glu | Val |
| Glu 545 | Tyr | Ile | Val | Asn | Asn 550 | Lys | Thr | Gly | Asn | Pro 555 | Val | Leu | Phe | Ala | Val 560 |
| Glu | Leu | Asn | Val | Ala 565 | Val | Gln | Ser | Ile | Met 570 | Glu | Ser | Pro | Gly | Val 575 | Leu |
| Arg | Gly | Lys | Glu 580 | Ile | Val | Val | Asp | Asp 585 | Lys | Tyr | Ala | Val | Gly 590 | Lys | Phe |
| Ala | Leu | Lys 595 | Phe | Glu | Asp | Glu | Met 600 | Glu | Val | Trp | Lys | Tyr 605 | Pro | Val | Lys |
| Thr | Leu 610 | Ser | Gln | Ser | Glu | Ser 615 | Gly | Trp | Asp | Leu | Ile 620 | Gln | Gln | Gly | Val |
| Ser 625 | Tyr | Ile | Val | Pro | Ile 630 | Arg | Leu | Glu | Asp | Lys 635 | Ile | Arg | Phe | Lys | Leu 640 |
| Lys | Phe | Glu | Glu | Ala 645 | Ser | Gly | | | | | | | | | |

α-AMYLASE GENE

TECHNICAL FIELD

The present invention relates, in general, to a cloned α-amylase gene, and, in particular, to a cloned hyperthermophilic α-amylase gene and to methods of producing α-amylase using same.

BACKGROUND OF THE INVENTION

Alpha-amylases are widely distributed throughout nature. The activity of α-amylase is characterized by the hydrolysis of α-1,4 glucosidic bonds in an endo-fashion, in a process known industrially as liquefaction. Due to the high viscosities and mass transfer problems, industrial liquefaction is carried out at the highest possible temperature. Typically, using the α-amylase from *B. licheniformis*, the starch slurry along with calcium ions are incubated at 100° C. for 5 to 10 minutes then kept at 95° C. for 1 to 2 hours (Ng, T. K., and W. F. Keneally in *Thermophiles: General, Molecular and Applied Microbiology*, T. D. Brock, ed., John Wiley & Sons, New York (1986)). This process is essential for several industries. Glucopolymers with varying degrees of polymerization are utilized in papermaking, textile preparation, brewing and fermentation. Liquefaction is a preliminary step in saccharification by which large quantities of D-glucose can be produced from inexpensive sources.

Thermostable α-amylases are well suited for the elevated temperatures used in industrial liquefaction in that the more thermostable the enzyme, the more efficient the hydrolysis at extreme temperature. The enzymes isolated from thermophilic microorganisms display inherent thermostability comparable to their optimal growth temperature. Thus, the higher the optimal growth temperature of the microorganism, the greater the likelihood that it will produce an α-amylase suitable for industrial application.

Many α-amylases have been purified which display thermostable characteristics. These range from moderate thermophiles, with optimal enzymatic activities within the range of 50° to 80° C. (Antrankian, *Applied Biochem. Biotech.* 20/21: 267 (1989), Glymph and Stutzenberger, *Applied Environ. Microbiol.*, 34: 391 (1977), Hasegawa et al, *J. Biochem*, 79: 35 (1976)), to hyperthermophiles with optimal activities above 80° C. (Schumann et al, FEBS, 282: 122 (1991), Koch et al, *Arch. Microbiol*, 155: 572 (1991), Laderman et al (1992)). α-Amylases isolated from microorganisms with optimal growth temperatures at or near 100° C. have been found to have optimal activities at this temperature, with residual activity at temperatures as high as 120° C., making them ideally suited for industrial application.

Using genetic engineering technology, it is theoretically possible to clone genes and produce the enzymes that they encode in quantities sufficient for industrial application. A number of genes coding for thermophilic α-amylases have been isolated and subsequently expressed in *E. coli* and *B. subtilis* (Fukusumi et al, Eur. J. Biochem., 98: 95 (1985), Tsukagoshi et al, Mol. *Gen. Genet.*, 195: 58 (1984), Tsukagoshi et al, *J. Bacteriology*, 164: 1182 (1985)). The temperature at which the genes are endogenously translated does not seem to have an effect on the expression in transformation competent cells. Thus it is possible to produce thermophilic enzymes in host cells grown at ambient temperature. However, no genes coding for hyperthermophilic α-amylases have ever been successfully cloned.

The hyperthermophilic archaebacterium *Pyrococcus furiosus* has been isolated from solfateric mud and found to have an optimal growth temperature of 100° C. (Fiala and Stetter, *Arch. Microbiol.*, 145: 56 (1968)). α-Amylase activity from *P. furiosus* has been detected in the cell-free supernatant (Antrankikian et al, WO 90/11352, (1990)), and in crude cell extract (Brown et al, *Appl. Environ. Microbiol.*, 56: 1985 (1990)). The α-amylase derived from this bacterium is known to be stable at high temperature and is expected to be widely used in industrial fields. However, methods for the industrial production of this enzyme from *P. furiosus* are not established and neither the gene structure nor the amino acid sequence of this enzyme has been reported.

The present invention provides, for the first, time a cloned sequence encoding a hyperthermophilic α-amylase. The availability of this sequence makes possible the industrial scale production of this enzyme.

SUMMARY OF THE INVENTION

The present invention relates to an isolated DNA segment having a nucleotide sequence that encodes α-amylase, specifically, a hyperthermophilic α-amylase. The invention further relates to a recombinant method of producing hyperthermophilic α-amylase. The invention also relates to an expression vector suitable for use in such a method.

It is a general object of the invention to provide a gene encoding a hyperthermophilic α-amylase.

It is a specific object to provide a gene encoding α-amylase from *P. furiosus*.

It is another object of the invention to provide a recombinant DNA molecule comprising a vector and the above-described gene, and to provide a host cell containing same.

It is a further object of the invention to provide a method of producing hyperthermophilic α-amylase.

Additional objects and advantages of the invention will be clear from a reading of the description that follows.

BRIEF DESCRIPTION OF THE DRAWINGS

FIG. 1: Nucleotide sequence of the PstI-HindIII fragment carrying the α-amylase gene (SEQ ID NO: 1). Sequences of the primer 1 and primer 2 are underlined. The amino acid sequence which was coincident with that deduced from the nucleotide sequence of the amplified fragment is encompassed by a square. The α-amylase produced in *E. coli* cells carrying pKENF-NH has two additional residues, Met and Gly, at the amino terminus (SEQ ID NO: 2) of its counterpart purified from the cell extract of *P. furiosus* (SEQ ID NO: 8) because of the introduction of the recognition sequence of NcoI in the expression vector.

FIG. 2: Restriction map of the PstI fragment encoding the α-amylase

DETAILED DESCRIPTION OF THE INVENTION

Figure 3:
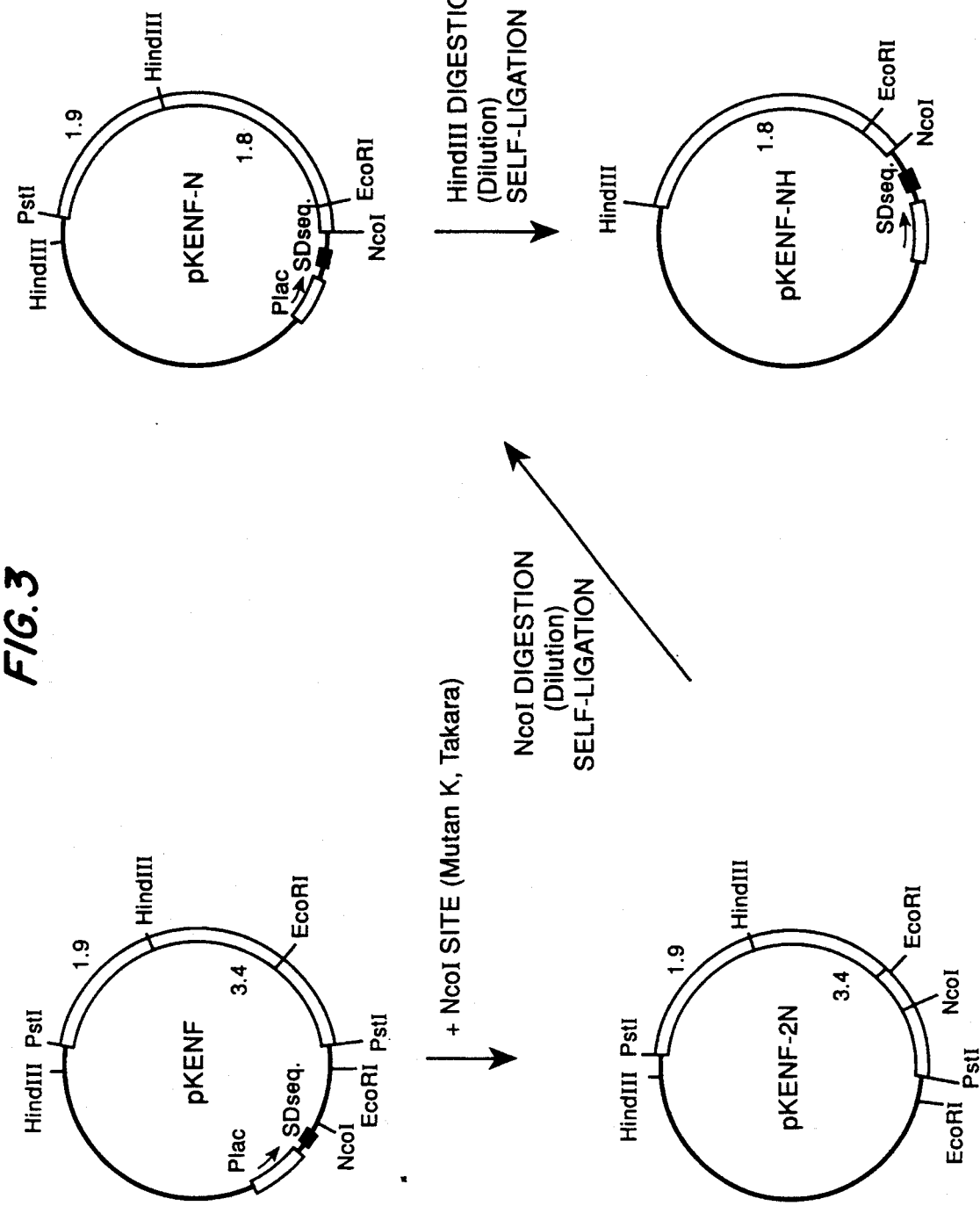
FIG. 3: Structure and construction of an expression plasmid pKENF-NH

The invention relates to an isolated DNA segment encoding all, or a portion, of α-amylase from a hyperthermophilic bacteria, preferably an archaebacterium, most preferably *P. furiosus*. The invention also relates to a recombinant molecule containing such a DNA segment, and to cells transformed therewith. In a further embodiment, the present invention relates to a method of producing hyperthermophilic α-amylase.

The DNA segment to which the invention relates, which can be a cDNA sequence, can encode the entire amino acid sequence given in FIG. 1 (the specific DNA sequence given in FIG. 1 being only one example), or a portion thereof of at least 15 amino acids (corresponding to 45 nucleotides), preferably at least 25 amino acids (corresponding to 75 nucleotides), more preferably at least 35 amino acids (corresponding to 105 nucleotides), and most preferably at least 75 amino acids (corresponding to at least 225 nucleotides). One skilled in the art will appreciate that these portions have utility, for example, as probes. DNA segments to which the invention relates also include those encoding proteins (or polypeptides) having substantially the same enzymatic activity of α-amylase of *P. furiosus* (for example, functionally equivalent allelic or species variations of the amino acid sequence of FIG. 1).

The present invention also relates to a recombinant DNA molecule that includes a vector and a DNA segment as described above (advantageously, a DNA segment encoding the protein shown in FIG. 1). The vector can take the form of a virus or a plasmid vector. Examples of such vectors include, for example, derivatives of the λ phage or of the pUC plasmid (e.g. pUC18 and pUC 19) and pET vectors. The DNA segment can be present in the vector operably linked to regulatory elements, including, for example, a promoter (for example, a heat shock promoter). Promoters appropriate for use in the present method include promoters functional in eubacteria, for example *E. coli* or *B. subtilis*, or in eucaryotes, for example, yeasts. The recombinant molecule of the invention can be suitable for transforming procaryotic or eucaryotic cells.

In a further embodiment, the present invention relates to a host cell transformed with the above-described recombinant molecule. The host can be procaryotic (for example, bacterial, such as *E. coli* and *B. subtilis*), lower eucaryotic (i.e., fungal, including yeast) or higher eucaryotic (i.e., mammalian). Transformation can be effected using method known in the art. When the recombinant molecule takes the form of an expression system, the transformed cells can be used as a source for the above-described protein.

The Examples that follow make reference to the hyperthermophilic bacteria, *P. furiosus* (deposited at Deutsche Sammlung von Mikroorganismen with the identification number of DSM 3638). The procedures for cloning the α-amylase gene from this bacteria and for preparing transformants carrying the gene, can be described in general terms as follows:

1. α-Amylase is purified from a cell extract of *P. furiosus*.
2. Partial amino acid sequences of the enzyme obtained in step (1) above is determined by the Edman method.
3. Chromosomal DNA is extracted from *P. furiosus*.
4. Oligodeoxyribonucleotide primers are synthesized for gene amplification based on the amino acid sequences obtained in step (2) above, and amplification by PCR is carried out using two of these primers and chromosomal DNA obtained in step (3) above as a template.
5. Chromosomal DNA obtained in step (3) above is digested with an appropriate restriction enzyme; the digest is separated by agarose gel electrophoresis, and transferred to a membrane. The amplified DNA obtained in step (4) is labeled and hybridization is carried out. DNA fragments (the sizes of which are estimated from the hybridization) are recovered from the gel.
6. Vector DNA is cut with an enzyme at a unique site and the DNA fragments obtained in step (5) above are inserted.
7. The DNA fragments inserted into the vector are introduced into a host cell and a transformant carrying the target sequence (sequence encoding the α-amylase) is selected.
8. Plasmid DNA is extracted from the transformant selected in step (7) above.
9. The sequence encoding α-amylase is operably linked to the translation signal (SD sequence) of a plasmid to construct an expression plasmid, from which translation occurs in the proper reading frame.
10. A 3'-noncoding sequence from the expression plasmid obtained in step (9) above is removed to produce another expression plasmid with higher expression level.
11. A host cell is transformed with the expression plasmid obtained in step (10) above.
12. The transformant obtained in step (11) above is cultured and α-amylase prepared from an extract of the cultured cells.

Purification of α-amylase from *P. furiosus* (DSM No. 3638) can be accomplished using the method of Laderman et al (1992), the technique entailing a series of successive chromatographic separations followed by reparative electroelution.

The α-amylase prepared by this method is a homodimer with a molecular weight of 130 kDa. The enzyme has a pH optimum within the range of 6 to 8 at 92° C., and displays significant activity and stability independent of calcium ions. Following incubation at 100° C. for three hours, the enzyme retains over 80% of its original activity.

Partial amino acid sequence information was obtained from purified α-amylase using the automated Edman method (Hunkapiller et al, Methods in Enzymology 91: 399 (1983). The N-terminal sequence of the intact protein is set forth below in Table 1 and is designated Sequence 1. The N-terminal sequence of one of the purified fragments, followed cyanogen bromide and trypsin digestion, is set forth in Table 1 and is designated Sequence 2.

TABLE 1

| PARTIAL AMINO ACID SEQUENCES OF α-AMYLASE |
|---|
| Sequence 1: DKINFIFGIHNHQPLGN |
| Sequence 2: TLNDMRQEYYFK |

Sequence 1 (SEQ ID N0:3) represents the amino terminal sequence of the α-amylase and sequence 2 (SEQ ID NO:4) represents that of one of the products digested by trypsin and cyanogen bromide.

Chromosomal DNA of *P. furiosus* can be extracted from a stationary culture of the organism at 100° C. Extraction, purification, and restriction enzyme digestion can be performed with methods known in the art and detailed in *Molecular Cloning, A Laboratory Manual* (Maniatis et al, Cold Spring Harbor Laboratory 1982, pages 75 to 178).

Primers 1, 2, and 3 in Table 2 below, were utilized in the cloning of the α-amylase gene. The primers were designed based on the partial amino acid sequence information obtained by the Edman method. It was found that a DNA fragment could be specifically amplified when the two-step PCR (nested PCR) was performed using these primers and chromosomal DNA of *P. furiosus* as a template. The nucleotide sequence of the amplified fragment (FIG. 1) was identified, and possible amino acid sequences, which could be encoded by the fragment, were deduced. The amino acid sequence of sequence 1 (Table 1), which was obtained by the Edman method, was found in one of the amino acid sequences deduced. Thus the DNA fragment encoding the α-amylase amylase gene was cloned using the amplified DNA fragment as a probe.

TABLE 2

SEQUENCES OF THE PCR PRIMERS
USED FOR PROBE PREPARATION

Primer 1:  5'GATAAAATTAATTTTATTTT 3'
              C  G  C  C  C  C
                    A        A Primer 2:  5'TGGTATTCATAATCATCAACC 3'
              C  C  C  C  C  C  G
                    A  A
                    G Primer 3:  5'TTTAAAATAATATTCTTGACTCATATCATT 3'
              C  G  G  G  C  C  GG    G  G
                                 T
                                 C Primer 1 (SEQ ID NO:5) and primer 2 (SEQ ID NO:6) were designed based on the sequence 1 and primer 3 (SEQ ID NO:7) was designed based on sequence 2.

The method of cloning the α-amylase gene can be described generally as follows.

Southern hybridization is performed and the restriction enzyme map of the chromosomal DNA surrounding the coding sequence of the α-amylase gene established using PstI, HindIII, XhoI, and EcoRI to digest chromosomal DNA of *P. furiosus*. Based on the restriction map obtained (see FIG. 2) a restriction fragment containing the entire α-amylase gene can be obtained and inserted into a plasmid vector. For this purpose, any of a number of available plasmid vectors can be used, for example, pUC18, pUC19, pTV118N, and pTV119N. Methods of insertion are known in the art.

Wild type or genetically modified strains of, for example, *Escherichia coli*, can be used as a host. However, it is preferable to use a strain that is deficient in restriction and normal in modification (r−, m+). DNA can be introduced into a host using a known method, such as that described at page 250 of *Molecular Cloning*, A Laboratory Manual, referenced above. *E. coli* cells carrying the plasmid DNA (transformants) can be selected based on a marker gene present in the vector used. For example, when pTV118N is used as a vector, cells carrying the plasmid can be obtained by selection of colonies that are resistant to ampicillin.

Next, transformants carrying the α-amylase gene are selected. Selection is done either by colony hybridization or plaque hybridization according to the characteristics of the vector used, as is known in the art.

The procedures described above were followed, and a plasmid that had a PstI fragment carrying the entire α-amylase gene was obtained and inserted at a PstI site in the expression vector pTV118N. This plasmid is referred to below as pKENF.

*E. coli* was the host used as in the cloning studies described herein, but in principle any methophilic or even thermophilic bacteria, transformed with an appropriate vector, can be used as a host, for example *Bacillus subtilis* or *Bacillus brevis*.

Construction of an expression vector requires identification of the nucleotide sequence of the fragment carrying the α-amylase gene (FIG. 1). The recognition sequence of NcoI can be introduced near the 5'-end of the α-amylase gene such that the ATG initiation codon in the recognition sequence of NcoI is in frame. This process of site-directed mutagenesis can be done in a conventional way by use of either Mutan TM -K or Mutan TM -G (commercial products of Takara Shuzo), or can be done using PCR. In the studies involved in the present invention, Mutan TM -K was used to introduce the recognition sequence of NcoI in pKENF, giving pKENF-2N. The sequence between by the two NcoI recognition sequences, one on the vector sequence and another near the 5' end of the fragment of the α-amylase gene, can be deleted to obtain an expression plasmid; pKENF-N is such a plasmid. Expression from the α-amylase gene can be induced by IPTG when this gene is transcribed under the control of the promoter of lacZ gene.

In the studies that resulted in the present invention, a noncoding region of pKENF-N at the 3'-site of the α-amylase gene (between two HindIII sites) was deleted to obtain another expression plasmid with higher expression level. This expression plasmid is referred to as pKENF-NH below. Structures and a scheme for construction of plasmids pKENF, pKENF-2N, pKENF-N, and pKENF-NH are shown in FIG. 3.

*E. coli* cells carrying pKENF-NH were cultured, and a cell extract was obtained. Significant levels of α-amylase activity were found in the extract after heat treatment (100° C.) for 10 min. No activity was detected in the cell extract obtained from *E. coli* cells carrying the expression vector pTV118N.

*E. coli* JM109 cells were transformed with pKENF-NH and a vigorously growing transformant was deposited on Mar. 7, 1992, under the terms of the BUDAPEST TREATY, in the Fermentation Research Institute, Agency of Industrial Science and Technology, Japan with the name being *Escherichia coli* JM 109/pKENF-NH, Accession number FERM BP-3782.

Three hundred units of extremely thermostable α-amylase measured by the Caraway method (see below) were obtained from one milliliter of the culture of *E. coli* JM109/pKENF-NH, thus making possible production of the enzyme on an industrial scale.

Certain aspects of this invention will be explained in greater detail by reference to the following non-limiting Examples.

EXAMPLE 1

Purification of intracellular α-amylase from *P. furiosus* DSM 3638 and determination of partial amino acid sequence Bacteria were grown on a complex medium modified from that previously described by Blumentals et al. (Blumentals et al Applied and Environ. Micro. 56(7): 1992 (1990)) consisting of artificial seawater supplemented with 0.3% tryptone, 0.7% yeast extract, and 0.1% soluble potato starch. Medium was prepared and dispensed into two liter bottles and then autoclaved. Following sterilization, in addition to the supplemental salts described previously, elemental sulfur and sodium sulfite were added at 156 mM and 2 mM, respectively. Prior to cooling to below 90° C., the medium was purged with nitrogen, 1% volume of inoculum from a previously grown culture was added, and the bottles were sealed. The cultures were allowed to incubate at a constant temperature of 98° C. for 16 hours and were subsequently harvested. A typical volume of growth medium used for each incubation was 20 liters, providing cell yields of 0.7 to 1.0 g/liter (wet weight).

Purification was carried out as follows (A) Crude Extract. Cells were harvested from growth media at 7,000× g for 10 minutes (8000 RPM in a Beckman JA10 rotor). The supernatant was decanted and the pellet collected. The cells from 20 liters of growth medium were resuspended in a final volume of 15 ml of 50 mM sodium phosphate pH 5.5 and subsequently disrupted by sonication using a Sonifer Cell Disrupter, at 50% maximum intermittently for three minutes. The cytosolic fraction of the lysate was collected after ultracentrifugation at 95,800× g for 1 hour (35,000 RPM in a Beckman Ti 45 rotor). All subsequent purification procedures were carried out at room temperature; protein solutions were stored at 4° C.

(B) Ion Exchange #1. The cytosolic fraction was applied to a Q-sepharose column (1.5 cm in diameter with a bed height of 45.5 cm) preequilibrated with 50 mM sodium phosphate pH 5.5 (Buffer A). Under these conditions, the amylase activity bound to the column and was eluted using 50 mM sodium phosphate pH 5.5, 1M NaCl (Buffer B) with a 200 minute linear gradient (100% A to 100% B). Fractions were collected and the tubes containing amylase were identified by activity and pooled.

(C) Ion Exchange #2. The pooled sample was diluted with an equal volume of buffer A and reapplied to the column which had been reequilibrated with 85% buffer A, 15% buffer B. The sample was eluted with the buffer described above using a 195 minute linear gradient (85% A, 15% B to 40% A, 60% B). The fractions were again pooled based upon activity and dialyzed overnight against 50 mM sodium carbonate pH 10.3 (Buffer A').

(D) Ion Exchange #3. The dialyzed sample was applied to a Q-sepharose column (1.5 cm diameter with a bed height of 46.5 cm) preequilibrated with buffer A' and eluted with 50 mM sodium carbonate pH 5.5, 1M NaCl (Buffer B') utilizing a 200 minute linear gradient (100% A' to 100% B'). Fractions containing α-amylase activity were collected and pooled. The active pool was then concentrated in Centricon 30 microconcentrators at 3020× g (5000 RPM in a Sorvall SS34 rotor), in 20 minute intervals, until the total volume was less than 2 ml.

(E) Electroelution. Purification was completed by electroelution from native-PAGE using the Bio-Rad model 491 Prep Cell. The apparatus was assembled using the 28 mm inner diameter gel tube containing an 8% acrylamide gel, 6 cm in height with a 1 cm, 4% stacking gel prepared as described above. The cooling buffer flow was maintained at 100 ml/min; the continuous elution flow was approximately 1 ml/min. The sample was prepared in 2× native sample buffer and was loaded in a volume less than or equal to 2.5 ml. Electrophoresis was carried out at 40 mV constant current and fractions were collected at 2.5 minute intervals. The elution of the protein was monitored with an Isco flow-through absorbance detector at 280 nm, allowing the correlation of specific fractions collected with the elution of protein bands from the gel. α-Amylase-containing fractions were detected by activity and screened, using silver stained native-PAGE, for purity. The active fractions, shown to be pure with the level of resolution of the silver stain, were pooled as final product. To obtain partial amino acid sequences, purified enzyme was digested with cyanogen bromide and, following reduction and pyridylethylation, with trypsin, using a modification of the methodology of Stone et al (Stone et al Practical Guide to Protein and Peptide Purification for Microsequencing, Ed. Matsudaira, P.T. Academic Press, N.Y., pp. 33–47 (1989). The resulting fragments were then separated by gradient elution from 100% water containing 0.1% (v/v) trifluoroacetic acid (TFA) to 70% acetonitrile containing 0.1% (v/v) TFA on a Aquapore RP-300 reverse phase narrow-bore column (0.2 cm ×25 cm), utilizing a Dionex Al-450 BioLC system.

Amino acid sequence analysis was performed on a Porton Instruments Model 2020 off-line sequencer using standard program #1. PTH amino acid analysis was carried out on a Beckman System Gold system using a modified sodium acetate gradient program and a Hewlett-Packard narrow-bore C-18 column.

EXAMPLE 2

Preparation of chromosomal DNA from *P. furiosus*

*P. furiosus* cells were grown in 2L of culture medium as described in Example 1. The cells were harvested and suspended in 4 ml of a mixture containing 25% sucrose and 0.05M Tris-HC1 (pH 8.0). Then 800 μl of lysozyme (5 mg/ml) was added to the suspension. After incubation of the mixture for 1 hour at 20° C., 24 ml of SET solution (150 mM NaCl, 1 mM EDTA, and 20 mM Tris HCI (pH 8.0)) was added to it. Four milliliters of 5% SDS and 400 μl of proteinase K (10 mg/ml) were added, and the mixture was incubated for 1 hour at 37° C., was extracted with phenol-chloroform, and precipitated with ethanol. DNA was recovered by winding with a sterilized toothpick. These steps gave 3.2 mg of genomic DNA.

EXAMPLE 3

Preparation of a DNA probe by the polymerase chain reaction (PCR)

Five hundred ng of *P. furiosus* chromosomal DNA were used as the template with 100 pmol of primer 1 and 100 pmol of primer 3 (see Table 2). The PCR profile was 94° C. for 0.5 min, 40° C. for 2 min, and 72° C. for 2 min. Amplification was done for 35 cycles in a total volume of 100 μl. One μl of the reaction mixture was reamplified with primer 2 (see Table 2) and primer 3. The PCR profile was same as above, but the number of cycles was 30. Five microliters of this mixture was analyzed by agarose gel electrophoresis. A DNA fragment about 1 kilobase pairs long was specifically amplified. The amplified DNA fragment was given blunt ends and subcloned into the HincII site of pUC 18. The cloned plasmid was sequenced by the dideoxy method.

EXAMPLE 4

Analysis of chromosomal DNA by Southern hybridization

Five-μg portions of *P. furiosus* chromosomal DNA were digested with PstI, HindIII, or EcoRI and electrophoresed through an agarose gel. The DNA was transferred to a nylon membrane and hybridized to the DNA probe obtained in Example 3. The probe was radiolabled by the random primer method. Hybridization was done for 2 hours at 65° C. in a hybridization bag containing 6× SSC, 0.1% SDS, 5× Denhardt's solution, 100 μg/ml calf thymus DNA, and 1×10⁷ cpm/ml of ³²P-labeled probe. The membrane was washed for 40 min in a solution of 2× SSC and 0.1% SDS at 65° and then for 20 min in a solution of 0.5× SSC and 0.1% SDS at 65°. X-ray film was exposed to the membrane overnight to obtain an autoradiographic image. The PstI fragment 5.3 kb long, the HindIII fragment 3.1 kb long, the XhoI fragment 5.3 kb long, and the EcoRI fragments 0.7 kb and 2.4 kb long were found to be positive.

EXAMPLE 5

Cloning of the DNA fragment, which contains the α-amylase gene

For cloning of the 5.3-kb PstI fragment obtained in Example 4, 50 μg of *P. furiosus* chromosomal DNA was digested with PstI. The digest was separated by agarose gel electrophoresis, and DNA fragments about 5.3 kb long were purified from the gel. Plasmid pTV118N was digested with PstI and dephosphorylated, and the DNA fragments about 5.3 kb long were ligated to the plasmid DNA with T4 DNA ligase. The ligation mixture was used to transform *E. coli* JM109 cells. Recombinant plasmids containing the target sequence were screened for by colony hybridization. Briefly, 349 colonies were transferred to nylon membrane. The colonies were lysed with 0.5N NaOH and 1.5M NaCl and the membrane was neutralized with 1M Tris-HCl (pH 7.0) containing 1.5M NaCl. Then the DNA was fixed to the membrane by ultraviolet irradiation. Preparation of the DNA probe and the conditions of hybridization were as described in Example 4. The plasmid obtained from one of the three positive clones was designated pKENF.

EXAMPLE 6

Construction of pKENF-HN, which expresses α-amylase

FIG. 3 shows the process of construction of the plasmid pKENF-HN. First an NcoI site was created near the translation initiation codon of the α-amylase gene in the plasmid pKENF obtained in Example 5 with use of a kit (site-directed mutagenesis system Mutan ™-K; Takara Shuzo). This plasmid (pKENF-2N) was digested with NcoI and self-ligated to eliminate an extra 5'-noncoding region. The resulting plasmid (pKENF-N) was digested with HindIII and self-ligated to delete a 3'-noncoding region. This recombinant plasmid was designated pKENF-NH.

*E. coli* JM109 cells carrying this plasmid were named *E. coli* JM109/pKENF-HN and were deposited at the Fermentation Research Institute, Agency of Industrial Science and Technology, Japan, as FERM BP-3782.

EXAMPLE 7

Preparation of crude cell extract and assay of α-amylase activity

*E. coli* JM 109/pKENF-NH cells obtained in Example 6 were grown for 15 hours at 37° C. in 5 ml of L broth containing 100 μg/ml ampicillin. The cells were then collected from 1 ml of the culture, suspended in 200 μl of a lysis solution (50 mM Tris-HCl (pH 7.6), 2 mM mercaptoethanol, 10% glycerol, 4 mM p-amidinophenyl-methanesulfonyl fluoride, and 0.1 mg/ml lysozyme), and incubated for 60 min at 37° C. The mixture was then sonicated and centrifuged. The supernatant was incubated for 10 min at 99° C. and centrifuged again. This supernatant was used as the crude cell extract.

e-Amylase activity was measured following Caraway, W. T. (American Journal of Clinical Pathology, 32: 97–99, 1959) with an amylase assay kit (Amylase Test Wako; Wako Pure Chemicals, Japan). Briefly, 20 μl of the crude cell extract obtained as described above was added to 1 ml of the buffer containing soluble starch, which had been pre-warmed for 5 min at 90° C. After incubation at 90° C., the reaction mixture was mixed with 1 ml of a chromogenic reagent and 5 ml of distilled water. The absorbance at 660 nm was measured and the αamylase activity (Caraway unit) was calculated with the following equation:

$$\text{Activity (Caraway unit)} = (E_{B1} - E_S)/E_{B1} \times 800,$$

where Es is a measured value when a sample solution is used and $E_{B1}$ is that when distilled water is used in place of the sample solution (enzyme blank). From 1 ml of the culture medium, 300 units of αamylase was obtained.

The contents of all references cited hereinabove are incorporated herein by reference.

One skilled in the art will appreciate from a reading of this disclosure that various changes can be made in form and detail without departing from the true scope of the invention. In this regard, one skilled in the art will appreciate that the concept of placing a gene sequence derived from *P. furiosus* under control of a promoter distinct from the *P. furiosus* endogenous promoter can be applied to sequences encoding *P. furiosus* proteins other than α-amylase, including, for example, sequences encoding pullulanase, α-glucosidase, β-glucosidase and proteases. In so doing, it is expected that expression of *P. furiosus* proteins can be obtained in, for example, species of Escherichia and Bacillus.

---

What is claimed is:

1. A DNA fragment encoding Pyrococcus furiosus α-amylase which has the amino acid sequence shown in FIG. 1 (SEQ ID NO: 8).

2. A DNA fragment consisting of a polynucleotide that encodes *Pyrococcus furiosus* α-amylase which has the amino acid sequence shown in FIG. 1 (SEQ ID No: 8), or portion thereof encoding at least 15 consecutive amino acids.

3. A recombinant DNA molecule comprising:
   (i) a vector, and
   (ii) said DNA fragment according to claim 1 or 2.

4. The recombinant DNA molecule according to claim 3, wherein said vector is a plasmid vector.

5. The recombinant DNA molecule according to claim 3, wherein said DNA fragment is operably linked to a promoter.

6. The recombinant DNA molecule according to claim 5, wherein said promoter is a promoter distinct from that naturally associated with the DNA fragment.

7. The recombinant DNA molecule according to claim 6 wherein said promoter is functional in eubacteria.

8. A host cell transformed with the recombinant DNA molecule according to claim 3.

9. The host cell according to claim 8, wherein said cell is a prokaryotic cell.

10. The host cell according to claim 8, wherein said host cell is an Escherichia or Bacillus cell.

11. A process of producing hyperthermophilic α-amylase comprising culturing the host cell according to claim 8 under conditions such that said DNA fragment is expressed and said α-amylase is thereby produced.

12. A process of producing α-amylase of *Pyrococcus furiosus*, comprising the steps of:
   (i) operably linking a DNA fragment consisting of a nucleotide sequence encoding said α-amylase to a promoter that is distinct from that naturally associated with said DNA fragment and that is effective for directing the synthesis of mRNA that can be translated to produce said protein in a host cell, whereby a cassette is formed;
   (ii) introducing said cassette into said host cell; and
   (iii) incubating said host cell resulting from step (ii) under conditions such that said DNA fragment is expressed and said protein is thereby produced;
   said α-amylase having the amino acid sequence shown in FIG. 1 (SEQ ID NO: 8).

13. The process according to claim 12, wherein the host cell is Escherichia or Bacillus.

* * * * *